United States Patent [19]

Shen et al.

[11] Patent Number: 4,910,325

[45] Date of Patent: Mar. 20, 1990

[54] POLYMERIZABLE QUATERNARY AMMONIUM METHYL CARBONATES

[75] Inventors: Thomas C. Shen, Chesapeake; James H. Rea, Portsmouth, both of Va.

[73] Assignee: Hoechst Celanese Corporation, Somerville, N.J.

[21] Appl. No.: 301,068

[22] Filed: Jan. 25, 1989

[51] Int. Cl.$^4$ .............................................. C07C 87/30
[52] U.S. Cl. ................................................... 558/260
[58] Field of Search ......................................... 558/260

[56] References Cited

FOREIGN PATENT DOCUMENTS 1208151 7/1986 Canada .

Primary Examiner—Joseph L. Schofer
Assistant Examiner—Alex H. Walker
Attorney, Agent, or Firm—Depaoli & O'Brien

[57] ABSTRACT

In one embodiment this invention provides a novel polymerizable quaternary ammonium carbonate corresponding to the formula:

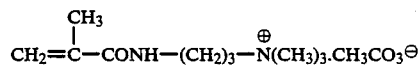

In another embodiment this invention provides a novel copolymer of the above represented methacrylamidopropyltrimethylammonium methyl carbonate and acrylamide, which exhibits a high level clay flocculation efficiency.

3 Claims, No Drawings

POLYMERIZABLE QUATERNARY AMMONIUM METHYL CARBONATES

BACKGROUND OF THE INVENTION

Polymerizable quaternary ammonium salts are important monomers for the production of water-soluble cationic polymers. The cationic polymers have significant utility as flocculants and retention auxiliaries in manufacturing operations such as the production of paper.

Among the widely used cationic monomers are methacrylamidoalkyl-trialkylammonium chlorides such as methacrylamidopropyltrimethylammonium chloride, as described in U.S. Pat. Nos. 4,460,758; 4,461,884; 4,556,736; 4,590,249; and 4,608,425.

A quaternary ammonium salt such as methacrylamidopropyltrimethylammonium chloride or the corresponding ammonium sulfate derivative are synthesized by methylating N-(3-dimethylaminopropyl)methacrylamide with either methyl chloride or dimethyl sulfate. The production of these quaternary ammonium salts requires specialized facilities since both methyl chloride and dimethyl sulfate are highly toxic reagents. Also, the resultant polymerizable quaternary ammonium salts exhibit corrosive properties and require special handling and storage.

The present invention embodiments were developed to overcome the deficiencies of the commercial type of polymerizable quaternary ammonium salts. Pertinent technical literature with respect to the present invention is that relating to quaternary ammonium carbonates, such as disclosed in U.S. Pat. No. 2,635,100 and Bull. Chem. Soc. Jap., 42, 1948 (1969).

Accordingly, it is an object of this invention to provide a novel polymerizable quaternary ammonium salt which is synthesized from low toxicity reactants.

It is another object of this invention to provide a novel acrylamidoalkyl-trialkylammonium salt which is non-corrosive, and which can be copolymerized with acrylamide to form a copolymer with superior flocculation efficiency as compared to commercial flocculants.

Other objects and advantages of the present invention shall become apparent from the accompanying description and examples.

DESCRIPTION OF THE INVENTION

One or more objects of the present invention are accomplished by the provision of a novel quaternary ammonium salt corresponding to the formula:

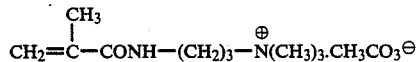

Example I hereinbelow illustrates that the synthesis of methacrylamidopropyltrimethylammonium methyl carbonate salt by a conventional procedure produces a product mixture which has a content of crosslinked polymeric byproduct.

The difficulties of synthesizing an invention quaternary ammonium salt compound were resolved by the development of a novel synthesis process which comprises (1) heating a solution of N-(3-dimethylaminopropyl)methacrylamide and dimethyl carbonate in a molar ratio of 1:1.2–1:2.5 at a temperature of about 85°–120° C. for a period between about 3–12 hours; (2) diluting the reaction product medium with water to form an aqueous solution having an organic concentration between about 40–70 weight percent, while maintaining the medium at a temperature between about 60°–100° C. during the water addition period; and (3) cooling the medium to ambient temperature to provide an aqueous solution of quaternary ammonium salt product.

The new process involves several critical aspects which affect the yield and quality of the final product.

Thus, if any organic solvent such as methanol, dimethylformamide, dimethylsulfoxide or tetrahydrofuran is utilized as a reaction medium during the synthesis process the reaction rate is reduced. The reaction rate also is lowered if the molar ratio of N-(3-dimethylaminopropyl)methacrylamide to dimethyl carbonate is less than about 1:2.5.

A molar ratio of N-(3-dimethylaminopropyl)methacrylamide to dimethyl carbonate which is higher than about 1:1.2 causes the production of a large quantity of oligomers. The production of oligomers also is promoted by reaction temperatures higher than about 120° C.

A particularly significant feature of the invention process is the step(2) dilution of the reaction product medium with water while the medium is maintained at a temperature between about 60°–100° C. As demonstrated in Example I, if the step(2) water dilution procedure is not practiced, the final product mixture will contain a gel-like solid of crosslinked polymer byproduct.

Other advantages derive from the novel invention process and novel quaternary ammonium methyl carbonate product. First, dimethyl carbonate reactant has low toxicity in comparison with methyl chloride and dimethyl sulfate. Second, the invention quaternary ammonium methyl carbonate product does not exhibit corrosive properties, since methyl carbonate anion is relatively pH basic in comparison with chloride and sulfate anions. Third, the invention quaternary ammonium methyl carbonate product can be copolymerized to form copolymers which exhibit superior flocculation properties in comparison with a commercially available cationic flocculant.

In another embodiment this invention provides a water-soluble polymer which is characterized by a recurring monomeric unit corresponding to the formula:

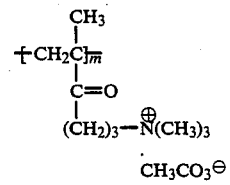

where m is an integer with a value of at least about 10.

A typical invention polymer has an intrinsic viscosity ($\eta$) in the range between about 1–3 dl/g.

A present invention water-soluble polymer can be a homopolymer, or it can be a copolymer in which methacrylamidopropyltrimethylammonium methyl carbonate is copolymerized with one or more polymerized vinyl monomers such as acrylamide, methacrylamide, N,N-dialkylacrylamide, N,N-dialkylmethacrylamide, acrylic acid, methacrylic acid, alkyl acrylate, alkyl methacrylate, acrylonitrile, vinylpyrrolidone, styrene, metal styrene sulfonate, vinyl acetate, vinyl chloride, vinyl alkyl ether, and the like. The quaternary ammonium methyl carbonate monomer can constitute between about 5-90 molar percent of a copolymer.

The preparation of the invention homopolymer proceeds readily with conventional polymerization methods. The preparation of an invention copolymer containing acrylamide monomer is not amenable to conventional solution or inverse emulsion polymerization conditions. It has been found that acrylamide-containing copolymer production requires a controlled combination of conditions to prevent the formation of an intractable crosslinked polymer product.

As demonstrated in Example IVA, an excellent copolymer of methacrylamidopropyltrimethylammonium methyl carbonate and acrylamide can be obtained in a quantitative yield by utilizing an organic solvent medium such as t-butanol, an aqueous solution of the quaternary ammonium carbonate monomer, slow addition of a free radical initiator such as 2,2'-azobis(2,4-dimethylvaleronitrile) or benzoyl peroxide, and a temperature of 65°-75° C.

In a further embodiment this invention provides a novel copolymer which exhibits superior clay flocculation properties in comparison with a commercial type of cationic flocculant.

Example V demonstrates that an invention copolymer of methacrylamidopropyltrimethylammonium methyl carbonate has an exceptional level of clay flocculation efficiency in comparison with a commercial type copolymer of methacrylamidopropyltrimethylammonium chloride and acrylamide.

The following examples are further illustrative of the present invention. The components and specific ingredients are presented as being typical, and various modifications can be derived in view of the foregoing disclosure within the scope of the invention.

EXAMPLE I

This Example illustrates the preparation of methacrylamidopropyltrimethylammonium methyl carbonate salt in accordance with a conventional synthesis procedure.

A 250 ml three-neck flask equipped with a stirrer, thermometer and condenser was charged with N-(3-dimethylaminopropyl)methacrylamide (42.57 g, 0.25 mole) and dimethyl carbonate (45.04 g, 0.5 mole). An inert atmosphere was provided by constant nitrogen pure, and the mixture was heated to 90°-102° C.

After a reaction period of 10 hours, a small amount of sample was withdrawn and diluted to 5 wt/wt% with HPLC carrier solvent*. The diluted solution was injected into an HPLC 5 micron spherisorb ODS reverse phase column. The yield calculated from the reduction of the peak area of N-(3-dimethylaminopropyl)methacrylamide was 98%.
*One liter of solution (15/85 v/v%) of acetonitrile/water containing 1.08 g of octanesulfonic acid, 5 ml of tetramethylammonium hydroxide (1.0 molar solution) and 20 g of 1-butanol.

EXAMPLE II

This Example illustrates the preparation of methacrylamidopropyltrimethylammonium methyl carbonate salt in accordance with a novel synthesis procedure of the present invention.

A three-liter three-neck flask equipped with a stirrer, thermometer and condenser was charged with N-(3-dimethylaminopropyl)methacrylamide (638.70 g, 3.75 mole) and dimethyl carbonate (675.60 g, 7.50 mole). The mixture was heated to 100°-103° C. for 10 hours under nitrogen. A HPLC analysis indicated a yield of 99%.

The product medium was cooled to 70° C., and deionized water (694.3 g) was added. After the product medium was cooled to room temperature, the bottom aqueous layer was separated and vacuum stripped for 3 hours at 55° C. and 1 mm Hg. Additional deionized water was added to provide a 60 w/w% aqueous solution of methacrylamidopropyltrimethylammonium methyl carbonate salt. The aqueous solution was stable for over 1 year at room temperature.

EXAMPLE III

This Example illustrates the preparation of poly[methacrylamidopropyltrimethylammonium methyl carbonate].

A 60% aqueous solution of methacrylamidopropyltrimethylammonium methyl carbonate salt (50 g) as illustrated in Example II, and deionized water (21 g), were charged into a 250 ml three-neck flask equipped with a stirrer, addition funnel and condenser. Under nitrogen, the solution was heated to 70° C. for 0.5 hour, then ammonium persulfate (0.07 g in 5.3 g of deionized water) was added to the solution over a period of 45 minutes. After a 7 hour polymerization period, a 150 ml quantity of deionized water was added. The resultant solution was poured into 500 ml of acteone to precipitate the polymer product. After vacuum drying, a yield of 28.12 g of homopolymer was obtained, which had an intrinsic viscosity of 1.055 dl/g in 1M NaCl as measured with a Cannon-Fenske SR100 Viscometer.

The polymerization procedure was repeated employing 0.06 g of 2,2'-azobis(2-amidinopropane) hydrochloride (V50) in 8 ml of deionized water in place of ammonium persulfate.

The polymerization procedure was repeated employing methacrylic acid or vinylpyrrolidone as a comonomer, and the intrinsic viscosities of the homopolymer and copolymer products were measured.

TABLE 1

| Co-Monomer | Initiator | Molar Ratio Co-Monomer/ DMAPMA-DMC | Yield % | (η) dl/g |
|---|---|---|---|---|
| None | (NH$_4$)$_2$S$_2$O$_8$ | — | 92 | 1.055 |
| None | V50 | — | 80 | 2.76 |
| Methacrylic acid | (NH$_4$)$_2$S$_2$O$_8$ | 0.43/1 | 94 | 1.16 |
| Vinylpyrrolidone | V50 | 4/1 | 98 | 2.371 |

EXAMPLE IV

This Example illustrates the preparation of a copolymer of methacrylamidopropyltrimethylammonium methyl carbonate salt and acrylamide (1:7.3 molar ratio) in accordance with the present invention, and a copolymer of N-(3-trimethylaminopropyl)methacrylamide chloride and acrylamide (1:7.3 molar ratio).

A

A 250 ml glass resin kettle was charged with 11.3 g of methacrylamidopropyltrimethylammonium methyl carbonate (60% aqueous solution), 16.05 g of acrylamide and 100 ml of t-butanol. A 0.1 g amount of 2,2'-azobis(2,4-dimethylvaleronitrile) (Vazo 52) initiator in 8 ml of t-butanol was placed in an addition funnel. The resin kettle was immersed in a constant temperature oil bath, 65° C. Nitrogen was bubbled through the reaction medium for a half hour, then the initiator solution was added dropwise to the reaction medium. The total procedure time was 6 hours.

The copolymer was isolated by filtration, washed with acetone, and dried in a vacuum oven (<5 mm Hg) at 50° C. for 8 hours (100% yield). The intrinsic viscosity ($\eta$) of the copolymer as measured in 1M NaCl solution with a Cannon-Fenske SR100 Viscometer was 1.22 dl/g.

B

Following the same polymerization procedure described above, a copolymer of methacrylamidopropyltrimethylammonium chloride and acrylamide was prepared (100% yield), and the intrinsic viscosity ($\eta$) was 1.8 dl/g.

EXAMPLE V

This Example illustrates the clay flocculation efficiency of a present invention copolymer of N-(3-trimethylaminopropyl)methacrylamide methyl carbonate and acrylamide, in comparison with a commercially available type copolymer of methacrylamidopropyltrimethylammonium chloride and acrylamide.

A 0.05% kaolin solution in 0.001M to 0.2M sodium chloride and a 0.16% polymer solution was prepared. A 500 ml aliquot of kaolin solution was placed in each of six 2000 ml beakers and an appropriate amount of polymer solution was added. Each of the beakers was placed under a paddle of a multi-paddle stirrer and stirred at 100 rpm for 1 minute then at 60 rpm for 20 minutes. After another 2 minutes, 10 ml of kaolin solution was withdrawn. The % transparency of the solution medium was measured with a Bausch and Lomb Spectronic 20 at 720 nm wavelength.

The copolymers of Example IV, Sections A and B, were tested for flocculation efficiency in accordance with the above described procedure.

TABLE 2

| Polymer | ($\eta$) dl/g | *Amount Of polymer (μl) | Clearness (% Transparency At 720 nm) |
|---|---|---|---|
| A.[1] | 1.22 | 100 | 17 |
|  |  | 150 | 27 |
|  |  | 300 | 54 |
|  |  | 500 | 82 |
| B.[2] | 1.8 | 100 | 13 |
|  |  | 150 | 15 |
|  |  | 300 | 20 |
|  |  | 500 | 28 |

[1]Invention copolymer of methacrylamidopropyltrimethylammonium methyl carbonate/acrylamide(1:7.3).
[2]Commercial type copolymer of methacrylamidopropyltrimethylammonium chloride/acrylamide(1:7.3).
*0.16% copolymer in Millipore water.

What is claimed is:

1. A quaternary ammonium salt corresponding to the formula:

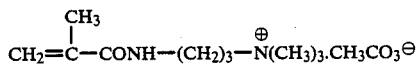

2. A process for producing methacrylamidopropyltrimethylammonium methyl carbonate salt which comprises (1) heating a solution of N-(3-dimethylaminopropyl)methacrylamide and dimethyl carbonate in a molar ratio of 1:1.2–1:2.5 at a temperature of about 85°–120° C. for a period between about 3–12 hours; (2) diluting the reaction product medium with water to form an aqueous solution having an organic concentration between about 40–70 weight percent, while maintaining the medium at a temperature between about 60°–100° C. during the water addition period; and (3) cooling the medium to ambient temperature to provide an aqueous solution of quaternary ammonium salt product.

3. An aqueous solution of quaternary ammonium salt produced in accordance with the process of claim 2.

* * * * *